(12) United States Patent
Park et al.

(10) Patent No.: US 10,092,698 B2
(45) Date of Patent: Oct. 9, 2018

(54) INJECTION GADGET

(71) Applicant: Daegu Gyeongbuk Institute of Science and Technology, Dalseong-gun, Daegu (KR)

(72) Inventors: Tae Sang Park, Daegu (KR); Dae Hyun Kum, Daegu (KR); Seong Hun Lee, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 36 days.

(21) Appl. No.: 15/582,873

(22) Filed: May 1, 2017

(65) Prior Publication Data
US 2017/0354780 A1 Dec. 14, 2017

(30) Foreign Application Priority Data

Jun. 8, 2016 (KR) ........................ 10-2016-0070699

(51) Int. Cl.
*A61M 31/00* (2006.01)
*A61M 37/00* (2006.01)
(Continued)

(52) U.S. Cl.
CPC ............ *A61M 5/2033* (2013.01); *A61B 34/30* (2016.02); *A61M 2005/206* (2013.01);
(Continued)

(58) Field of Classification Search
CPC .................. A61M 5/02; A61M 5/2033; A61M 2005/206; A61B 34/37
See application file for complete search history.

(56) References Cited

U.S. PATENT DOCUMENTS

| 4,394,863 A | 7/1983 | Bartner |
| 6,387,078 B1 | 5/2002 | Gillespie, III |

(Continued)

FOREIGN PATENT DOCUMENTS

| EP | 2 583 707 A1 | 4/2013 |
| KR | 20-0212566 Y1 | 2/2001 |

(Continued)

OTHER PUBLICATIONS

Korean Intellectual Property Office, Communication dated Aug. 22, 2017 in counterpart application No. 10-2016-0070699.
(Continued)

*Primary Examiner* — Edelmira Bosques
(74) *Attorney, Agent, or Firm* — Sughrue Mion, PLLC (57) ABSTRACT

Disclosed is an injection gadget corresponding to an end-effector such as a rescue robot or the like. The injection gadget is configured such that an injection needle is disposed inside an injection assembly, an injection liquid is provided between a cylinder and a piston of the injection assembly, and the piston is moved by an elastic force of a spring previously compressed inside the cylinder so that the injection needle protrudes to the outside of the injection assembly and the injection liquid is ejected, and includes a bracket that replaceably mounts the injection assembly, a main body that is connected to the bracket and includes a first body space portion of which one side surface facing the bracket and the other side surface are open to pass through each other and a second body space portion that is disposed next to the first body space portion, a controller that is mounted in the second body space portion, a linear actuator that moves a transfer shaft in accordance with a control signal of the controller, and a pusher that is disposed between the linear actuator and the injection assembly, and transmits a force of the linear actuator toward the injection assembly so that a
(Continued)

locking pin of the bracket is deviated from locking guides of the piston of the injection assembly.

9 Claims, 6 Drawing Sheets

(51) Int. Cl.
  *A61M 5/20* (2006.01)
  *A61B 34/30* (2016.01)
(52) U.S. Cl.
  CPC ............ *A61M 2005/208* (2013.01); *A61M 2005/2013* (2013.01); *A61M 2205/13* (2013.01); *A61M 2205/50* (2013.01); *A61M 2209/082* (2013.01)

(56) References Cited

U.S. PATENT DOCUMENTS

| | | |
|---|---|---|
| 2004/0054327 A1 | 3/2004 | Gillespie, III |
| 2009/0216182 A1 | 8/2009 | Lauchard et al. |
| 2010/0049126 A1* | 2/2010 | Bronfeld ................ A61F 7/02 604/113 |
| 2012/0071818 A1 | 3/2012 | Lauchard et al. |
| 2014/0243751 A1 | 8/2014 | Brereton et al. |
| 2014/0336578 A1 | 11/2014 | Brereton et al. |
| 2015/0190575 A1 | 7/2015 | Lauchard et al. |
| 2016/0151586 A1 | 6/2016 | Kemp |
| 2016/0375195 A1 | 12/2016 | Fabien |

FOREIGN PATENT DOCUMENTS

| | | |
|---|---|---|
| KR | 2003-0079937 A | 10/2003 |
| KR | 10-2013-0115938 A | 10/2013 |
| KR | 10-2016-0097417 A | 8/2016 |
| WO | 2007/088444 A1 | 8/2007 |
| WO | 2012/110576 A1 | 8/2012 |
| WO | 2015/055588 A1 | 4/2015 |

OTHER PUBLICATIONS

Korean Intellectual Property Office communication dated Nov. 29, 2017 in counterpart application No. 10-2016-0070699.

Tae Sang Park, et al., "Design of Operating Mechanism of the Injection Gadget for the Relief Work", 31st ICROS Annual Conference, Mar. 10, 2016, pp. 1-4.

* cited by examiner

INJECTION GADGET

CROSS-REFERENCE TO RELATED APPLICATION

This application claims priority to and the benefit of Korean Patent Application No. 10-2016-0070699, filed on Jun. 8, 2016, the disclosure of which is incorporated herein by reference in its entirety.

BACKGROUND

1. Field of the Invention

The present invention relates to an injection gadget, and more particularly, to an injection gadget which can be installed at an end of an automated robot such as a lifesaving robot, a rescue robot, etc., or can be applied as an end-effector for a robot.

2. Discussion of Related Art

In general, robots can be roughly classified into industrial robots and non-industrial robots when they are classified for each application among the classification standards of the International Federation of Robotics (IFR).

The industrial robots may precisely and stably perform tasks which are difficult for people to concentrate due to fatigue because they are static and repetitive for people to perform mainly in the manufacturing industry. These conventional industrial robots are configured to perform tasks in an isolated workspace called a factory site.

The non-industrial robots are also called service robots in other words, and provide useful services in human life. The non-industrial robots can be called robots that can be used in the same space with people due to the development of electric- and electronic-based technology, and much research is underway due to demands for them.

Especially in situations where it is difficult to commit people for rescue such as in natural disasters or wars, the necessity of technology development of rescue robots which are substituted for human beings to remotely check the condition of a person who needs a rescue and take emergency measures is highlighted.

However, an existing technology development focuses on identifying the condition of the person who needs a rescue and evacuating the person before taking emergency measures in case of human accident.

An injection device according to the prior art has an automatic injector type to easily decipher the blood contaminated by enemy CBR (chemical, biological, and radiological) attacks or paralysis of the nervous system in wartime situations.

For example, automatic injectors include aka MARK-1, ATNAA (antidote treatment nerve agent auto-injector), and the like.

MARK-1 is a system or kit for taking pyridostigmine tablets in advance prior to nerve agent addiction and administering MARK-1 and diazepam injections after addiction, and has been operated in the US military since the 1980s. That is, MARK-1 is a kit product consisting of a set of an atropine injector and a PAM injector.

ATNAA is an automatic injector product that enhances convenience by unifying an existing MARK-1 with two injectors into one injector.

An automatic injector product according to the prior art is used in a method in which a clip-type safety pin provided at the back of an injector is pulled out or a safety cap previously put on the injector is removed, and then the front end of the injector is placed perpendicular to a muscular part of the femoral region, pushed firmly into the same, and held for about 10 seconds to perform an injection.

An automatic injector according to the prior art associated with the above actual products is disclosed in U.S. Pat. No. 4,394,863. Here, the structure of the disclosed automatic injector implements the same mechanism as an automatic injector product (e.g., MARK-1, ATNAA, etc.) currently used for military use.

The operation mechanism of the prior art is described as follows. An injection needle is positioned inside a corresponding injection device in the front of the injector, an injection liquid is provided between a cylinder and a piston, and a safety pin or a safety cap is fitted behind the injection liquid.

When a user pulls the safety pin or the like out and firmly presses a button positioned at the back end of the automatic injector, the injection liquid is ejected simultaneously with protrusion of the injection needle due to a strong elastic force of a compressed spring at that moment.

Here, in order to perform relief activities related to the auto-injection, a process in which a person who needs a rescue or a rescuer holds the body of the automatic injector with one hand while pulling the safety pin of the automatic injector with the other hand is needed.

When this process is replaced by a rescue robot, an injection gadget additionally requires a structure to transmit power to an actuator for removing a safety pin in addition to an actuator for injection, thereby increasing a payload of a manipulator of the robot.

In addition, when the front of the automatic injector is pressed to perform relief activities, the elastic force of the compressed spring is generated inside the automatic injector in a process in which the manipulator presses the button of the automatic injector, the posture of the automatic injector is changeable by the generated elastic force, and thereafter the automatic injector having the changed posture slips so that it is difficult to maintain a perpendicular angle between the automatic injector and an injection site and also very difficult to accurately perform an injection on the injection site.

Accordingly, in situations where it is difficult to commit lifesaving manpower such as in natural disasters or wars, it is urgently necessary to develop an end-effector for a rescue robot which remotely checks the condition of a person who needs a rescue through the rescue robot and carries out emergency treatment while it is suitable for a rescue robot for evacuating the person who needs a rescue. In particular, technology development of an injection gadget miniaturized to reduce a payload of a manipulator which is a rescue robot is urgently needed.

SUMMARY OF THE INVENTION

The present invention is directed to an injection gadget which can release a locking pin and perform relief activities (e.g., injecting an injection liquid) at the same time by pressing a back region (e.g., a movable cap which is one end of an injection assembly) of an injection assembly using one linear actuator and one pusher without addition of a separate actuator for removing a safety pin and a driving unit, compared to an existing automatic injection device.

According to an aspect of the present invention, there is provided an injection gadget in which an injection needle is disposed inside an injection assembly, an injection liquid is provided between a cylinder and a piston of the injection assembly, and the piston is moved by an elastic force of a spring previously compressed inside the cylinder so that the injection needle protrudes to the outside of the injection assembly and the injection liquid is ejected, including: a bracket that replaceably mounts the injection assembly; a main body that is connected to the bracket and includes a first body space portion of which one side surface facing the bracket and the other side surface are open to pass through each other and a second body space portion that is disposed next to the first body space portion; a controller that is mounted in the second body space portion; a linear actuator that moves a transfer shaft in accordance with a control signal of the controller; and a pusher that is disposed between the linear actuator and the injection assembly, and transmits a force of the linear actuator toward the injection assembly so that a locking pin of the bracket is deviated from locking guides of the piston of the injection assembly.

Here, the main body may be connected to an end-effector connector of a manipulator having a rescue robot structure, and a connector of the main body may be electrically connected to the end-effector connector.

Also, the bracket may include a rear bracket and a front bracket which are disassembled or assembled for replacement of the injection assembly.

Also, the rear bracket of the bracket may include a pin holder that is inserted into the first body space portion and receives one end of the injection assembly, a first flange portion that is integrally formed on a rim of the pin holder, and a plurality of fastening pieces that protrude from a bottom surface of the first flange portion and have inclined steps.

Also, the front bracket of the bracket may include a second flange portion that includes fastening holes into which the fastening pieces are respectively inserted so that the second flange portion is caught by the inclined steps of the fastening pieces, an extension portion that extends from the second flange portion in a direction opposite to the first flange portion so as to mount the injection assembly, and a contact plate portion that is formed at an end of the extension portion and has a relatively large area as compared with the second flange portion.

Also, the contact plate portion may include a plurality of sensors that are provided on a surface of the contact plate portion facing an object to be injected and connected to the controller to detect a sensor value for estimating whether the object to be injected and the injection gadget are perpendicular to each other.

Also, the pin holder may include a hollow tube-shaped holder body that is penetratingly connected to a center hole of the first flange portion, a pin support portion that connects one side of an end of the holder body and the other side thereof to each other, pusher holes that are formed at both sides of the pin support portion to receive bottom protrusions of the pusher, and a locking pin that protrudes from an inner bottom surface of the pin support portion toward the injection assembly.

Also, the locking pin may pass through a pin hole formed in the injection assembly, and be sandwiched between the locking guides having an elastic stress to be pinched toward a center of the injection assembly so that the piston having the locking guides is brought into a locked state.

Also, the locking guides may include a plurality of guide bars that are cut or branched from one end of the piston of the injection assembly positioned below the pin hole so that the guide bars are bent radially outward according to contact with the locking pin or restored toward an inner center direction according to non-contact with the locking pin, and locking heads that are formed at ends of the guide bars so as to have an arrow shape, and the locking heads may be caught by a rim of a trigger hole of an inner cap positioned inside the injection assembly in response to a contact or non-contact situation with the locking pin, or are brought into a free state.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Advantages and characteristics of the present invention, and methods for achieving them will be apparent with reference to embodiments described below in detail in addition to the accompanying drawings. However, the present invention is not limited to the exemplary embodiments to be described below but may be implemented in various forms. Therefore, the exemplary embodiments are provided to enable those skilled in the art to thoroughly understand the teaching of the present invention and to completely inform the scope of the present invention, and the present invention is defined only by the scope of the appended claims.

Meanwhile, the terms used herein are for the purpose of illustrating the present invention only and should not be construed to limit the meaning or the scope of the present invention. As used in this specification, a singular form may, unless definitely indicating a particular case in terms of the context, include a plural form. Also, the expressions "comprise" and/or "comprising" used in this specification neither define the mentioned shapes, numbers, steps, operations, members, elements, and/or groups of these, nor exclude the presence or addition of one or more other different shapes, numbers, steps, operations, members, elements, and/or groups of these. Hereinafter, an embodiment of the present invention will be described in detail with reference to the accompanying drawings.

In the following embodiments of the present invention, since the facts that a piston moves by a strong elastic force of a spring previously compressed at the moment when a locking pin is released and an injection liquid is ejected simultaneously with protrusion of an injection needle are similar to the conventional automatic injector, description of components related to the protrusion of the injection needle and the ejection of the injection liquid will be omitted.

Figure 1:
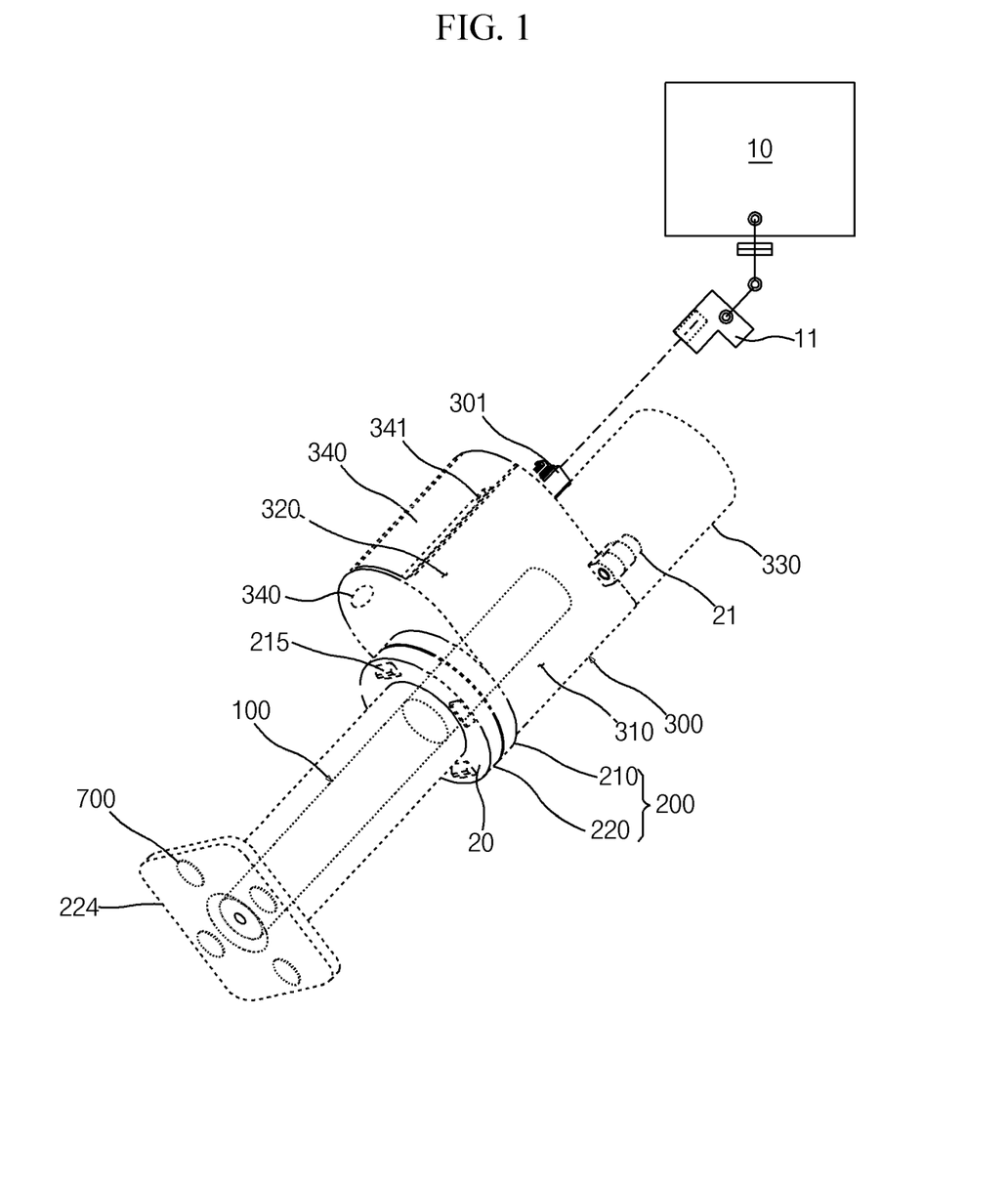
FIG. 1 is a perspective view showing an injection gadget according to an embodiment of the present invention.
Figure 2:
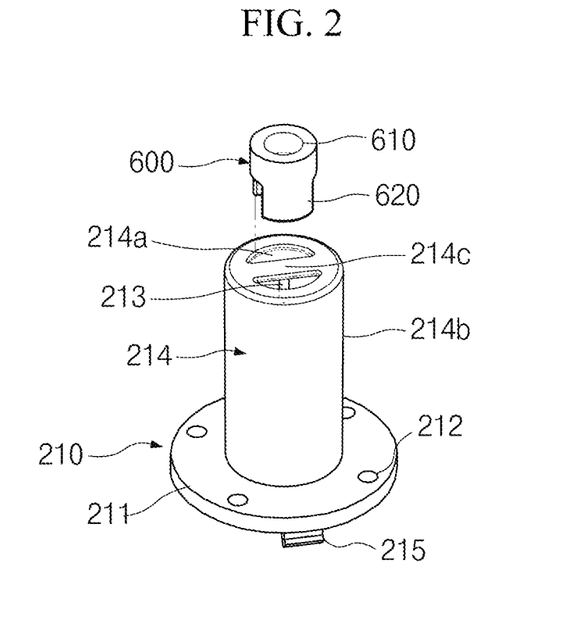
FIG. 2 is a perspective view showing a rear bracket and a pusher provided inside the injection gadget shown in FIG. 1.
Figure 3:
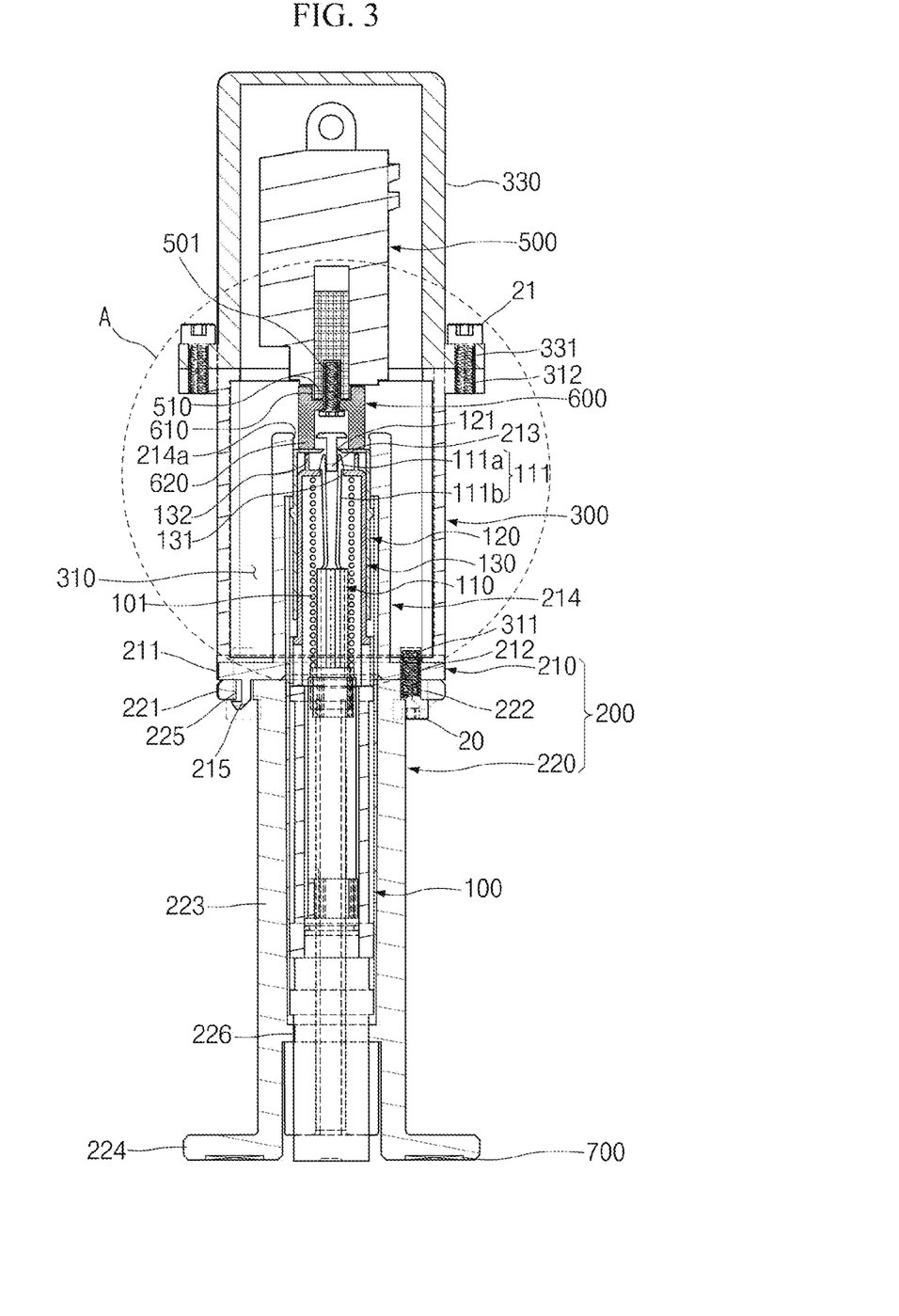
FIG. 3 is a coupled cross-sectional view showing the injection gadget shown in FIG. 1.

In the drawings, FIG. 1 is a perspective view showing an injection gadget according to an embodiment of the present invention, FIG. 2 is a perspective view showing a rear bracket and a pusher provided inside the injection gadget shown in FIG. 1, and FIG. 3 is a coupled cross-sectional view showing the injection gadget shown in FIG. 1.

Referring to FIGS. 1 to 3, the injection gadget according to the present embodiment includes an injection assembly 100, a bracket 200, a main body 300, a controller (not shown), a linear actuator 500, a pusher 600, and a sensor 700. The pusher 600 and a rear bracket 210 shown in FIG. 2 are coupled to the inside of the main body 300 of FIG. 1, and arrangement and coupling relationships of the pusher 600 and the rear bracket 210 can be clearly seen through FIG. 3. Here, the injection assembly 100 may be a component assembled within the injection gadget according to the present embodiment.

The overall shape of the injection gadget according to the present embodiment may not be limited to a specific shape because it can be designed in various forms as an end-effector.

The main body 300 of the injection gadget according to the present embodiment is connected to an end-effector connector 11 of a manipulator 10 having a rescue robot structure, and a connector 301 of the main body 300 is electrically connected to the end-effector connector 11.

The injection assembly 100 includes an injection needle (not shown) disposed therein in a manner similar to a general automatic injector. Here, an injection liquid is provided between a cylinder and a piston 110 inside the injection assembly 100. The piston 110 is moved by an elastic force of a spring 101 previously compressed inside the cylinder so that the injection needle protrudes to the outside of the injection assembly 100 and the injection liquid is ejected.

The bracket 200 replaceably mounts the injection assembly 100. To this end, the bracket 200 may be comprised of the rear bracket 210 and a front bracket 220 which are disassembled or assembled for replacement of the injection assembly 100.

The main body 300 is connected to the bracket 200. The main body 300 includes a first body space portion 310 of which one side surface facing the bracket 200 and the other side surface are open to pass through each other, and a second body space portion 320 that is disposed next to the first body space portion 310.

On a rim of the one side surface (the lower side in FIG. 3) of the first body space portion 310 of the main body 300, first bolt fastening holes 311 are formed to be respectively aligned with four bolt holes 212 of a first flange portion 211 of the rear bracket 210 of the bracket 200. Here, four front bolts 20 may pass through bolt holes 222 of a second flange portion 221 of the front bracket 220 and the bolt holes 212 of the first flange portion 211 and are coupled to the first bolt fastening holes 311 of the main body 300.

A first main body cover 330 for covering or protecting the linear actuator 500 is coupled to a rim of the other side surface (the upper side in FIG. 3) of the first body space portion 310 of the main body 300. For example, on the rim of the other side surface of the first body space portion 310 of the main body 300, second bolt fastening holes 312 are formed to be respectively aligned with four bolt holes 331 of the first main body cover 330. Four rear bolts 21 may respectively pass through the bolt holes 331 of the first main body cover 330 and be coupled to the second bolt fastening holes 312 of the main body 300.

In this manner, in the present embodiment, the first main body cover 330 and the bracket 200 are coupled to each other so as to be disassembled and assembled by the front bolt 20 or the rear bolt 21 with respect to the main body 300, so that assembly and maintenance of the linear actuator 500 or replacement of the bracket 200 equipped with the injection assembly 100 may be performed significantly easily.

The controller is mounted inside the main body 300, that is, inside the second body space portion 320. The second body space portion 320 may have an opening that is open in a direction in which the controller is mounted, and the opening of the second body space portion 320 may be closed by a second main body cover 340.

A laser pointer 340 for irradiating a laser beam is disposed inside or on a surface of a housing of the main body 300.

According to the present invention, an image for a scanning region on which the laser beam is irradiated by the laser pointer 340 or a region to be scanned is acquired using a camera for performing imaging on an object area to which a scanning assembly 100 is directed, and this camera is remotely controlled.

Since a position of the laser beam irradiated on the acquired image may be confirmed and a position of an injection point may be confirmed relative to the position of the laser beam, it is possible to inject an injection liquid through an injection needle at a position of the accurate injection point with respect to an object to be scanned.

A guide groove for cover insertion is further provided on the inner surfaces of both ends of the opening of the second body space portion 320 so that the second main body cover 340 may be opened and closed in a sliding door manner, thereby facilitating coupling of the second main body cover 340. The second main body cover 340 may further include a slit portion 341 formed in the longitudinal direction thereof. A user may visually recognize the inside of the second body space portion 320 through the slit portion 341. Here, the slit portion 341 can be used as a heat-releasing passage or a passage for extending an electric wire or a terminal when the slit portion 341 is configured to be opened as an elongated hollow space, and used as a check window when the slit portion 341 is clogged with a separate window (not shown) because it needs to be kept airtight. A slit-shaped opening (not shown) may be further provided on the wall of the main body 300 so as to be used for a purpose or application similar to that of the slit portion 341.

The controller includes a driving driver for controlling the travel speed and stroke of a transfer shaft 510 of the linear actuator 500. Here, the driving driver of the controller may include a communication module (not shown) configured to be interlocked with the operation of the manipulator 10, a sensor value input/output processing module (not shown), and the like, and be electrically connected to the linear actuator 500, the connector 301, and the sensor 700 (e.g., force sensor) which will be described later.

The linear actuator 500 serves to move (e.g., move forward or backward) the transfer shaft 510 in accordance with a control signal of the controller. Here, the movement of the transfer shaft 510 means a pushing operation of the linear actuator 500.

The pusher 600 is coupled to an end (e.g., a lower end) of the transfer shaft 510. As shown in FIGS. 3 to 6, the ends of the pusher 600 and the transfer shaft 510 may be interconnected by a connection bolt 501. The pusher 600 may be lowered or raised together with the transfer shaft 510.

The pusher 600 may be disposed between the linear actuator 500 and the injection assembly 100. The pusher 600 serves to transmit a force (e.g., a force for advancing or lowering the transfer shaft 510) of the linear actuator 500 toward the injection assembly 100 so that a locking pin 213 of the bracket 200 is deviated from locking guides 111 of the piston 110 of the injection assembly 100.

In the present embodiment, the locking guides 111 and the locking pin 213 may be protected in multiple by the rear bracket 210, the main body 300, and the like so that the structural safety and operational reliability of the injection assembly 100 of the rescue robot may be maximized.

The pusher 600 is a part of a trigger device of a releasing mechanism of the locking pin 213 as will be described in detail with reference to FIGS. 4 to 6, and causes the piston 110 of the injection assembly 100 which is in a locked state to be switched into a released state to correspond to the pushing operation (e.g., advancement of the transfer shaft 510) of the linear actuator 500. Here, the released state may mean a state in which the piston 110 initially fixed to the locking pin 213 can be freely moved by the elastic force of the spring 101.

That is, in the present embodiment, when the pusher 600 is pressed by the transfer shaft 510, the pusher 600 moves a movable cap 120 that is one end of the injection assembly 100, an inner cap 130, and the piston 110. As a result, the locking pin 213 of the bracket 200 can be in a relative movement state with respect to the movable cap 120, the inner cap 130, and the piston 110. Due to this relative movement, the locking pin 213 of the bracket 200 is deviated from the locking guides 111 of the piston 110. In this case, the locking guides 111, which have an elastic stress to be originally pinched, are restored to their original states, so that locking heads 111a of the locking guides 111 can be released as if they are pulled out of a rim of a trigger hole 131 of the inner cap 130.

The trigger hole 131 is positioned inside an upper portion of the inner cap 130, and has an inner diameter relatively smaller than a diameter of a gap retaining portion 132. In particular, at this time, the size of the inner diameter of the trigger hole 131 may be limited to a specific numerical value. Here, the specific numerical value of the trigger hole 131 may be selected and set within an inner diameter numerical value range in which the locking heads 111a in a state of being restored by the elastic stress and pinched so as to be in contact with each other can be passed through (see FIG. 6) the trigger hole 131, but the locking heads 111a can be fixed in such a manner that outer jaws of the locking heads 111a (see FIG. 4) in a state of being opened by contact with the locking pin 213 are caught by the trigger hole 131.

Referring to FIGS. 2 and 3, the rear bracket 210 of the bracket 200 includes a pin holder 214 that is inserted into the first body space portion 310 and receives one end of the injection assembly 100.

The rear bracket 210 includes the first flange portion 211 integrally formed on a rim of the pin holder 214 with respect to a lower side of the pin holder 214.

The rear bracket 210 includes a plurality of fastening pieces 215 protruding from a bottom surface of the first flange portion 211 and each having an inclined step.

A total of four fastening pieces 215 are formed on the bottom surface of the first flange portion 211 with respect to an outer periphery of the first flange portion 211. At this time, the fastening pieces 215 may be positioned at positions where they do not interfere with the bolt holes 212 of the first flange portion 211.

Here, the fastening pieces 215 may be used as a means for easily making the bracket 200 with the injection assembly 100 mounted thereon as a tentative assembly by coupling the rear bracket 210 and the front bracket 220 to each other before the bracket 200 is assembled to the main body 300 using the front bolt 20.

Next, the bracket 200 that is the tentative assembly is fixed or assembled to the main body 300 by the front bolt 20.

The front bracket 220 of the bracket 200 includes the second flange portion 221 having fastening holes 225 into which the fastening pieces 215 are respectively inserted so that the second flange portion 221 is caught by the inclined steps of the fastening pieces 215.

The front bracket 220 includes an extension portion 223 extending from the second flange portion 221 in a direction opposite to the first flange portion 211 so as to mount the injection assembly 100. The injection assembly 100 may be inserted and received through an inner space of the extension portion 223.

The front bracket 220 may further include a reinforcing ring portion 226 formed on an inner circumferential surface of the extension portion 223 with respect to a space between a contact plate portion 224 and the second flange portion 221.

The reinforcing ring portion 226 may increase the endurance rigidity of the extension portion 223 and serve as a stopper to prevent the injection assembly 100 from falling downward.

The front bracket 220 includes the contact plate portion 224 that is formed at an end of the extension portion 223 and has a relatively large area as compared with the second flange portion 221.

The extension portion 223 serves to support the contact plate portion 224 with respect to the main body 300 and surrounds the injection assembly 100 so that there is an advantage that the injection assembly 100 can be prevented partially from colliding against an external object to be broken.

The contact plate portion 224 and the extension portion 223 are connected to each other or formed integrally with each other while being kept at a right angle.

The contact plate portion 224 is formed to be relatively larger than the diameter of the injection assembly 100.

Accordingly, the contact plate portion 224 may be stably attached to an injection site, and consequently, according to the present embodiment, the contact plate portion 224 may help the injection site in maintaining a vertical angle.

In particular, a plurality of (e.g., four) of sensors 700 (e.g., force sensors) are provided on a surface of the contact plate portion 224 facing the injection site or an object to be injected.

Here, each sensor 700 is connected to the controller and detects a sensor value for estimating whether the object to be injected and the injection gadget are perpendicular to each other. That is, the detected sensor value may be input to the controller or transmitted to a control device of a manipulator connected to the controller.

An outer surface of each sensor 700 slightly more protrudes than the surface of the contact plate portion 224 so that it can be brought into contact with the injection site, the object to be injected or the like earlier than the contact plate portion 224.

The outer surface of each sensor 700 or the surface of the contact plate portion 224 may be further provided with a non-slip coating layer (not shown) made of synthetic rubber or soft synthetic resin, so that the perpendicular state between the object to be injected and the injection gadget may be maintained more stably.

Since the plurality of sensors 700 are arranged on a plane, for example, along an X-axis direction and a Y-axis direction, the control device of the manipulator may grasp or estimate an amount of contact force distribution corresponding to a sensor value for each position measured by each sensor 700. In this way, the control device of the manipulator may modify or correct a coordinate system of the injection gadget so that the injection gadget may perfectly maintain the perpendicular state with respect to the object to be injected, and therefore a sliding problem between the injection gadget and the object to be injected may be solved to accurately perform an injection on the object to be injected.

Meanwhile, the pusher 600 includes an insertion groove 610 into which the end of the transfer shaft 510 is inserted and two bottom protrusions 620 protruding in a direction opposite to the insertion groove 610.

A bolt hole through which a screw shaft portion of the connection bolt 501 passes and a support jaw to which a head of the connection bolt 501 is hooked are formed inside the insertion groove 610.

The bottom protrusions 620 of the pusher 600 are inserted into pusher holes 214*a* of the pin holder 214 of the rear bracket 210 (see FIG. 2).

Figure 4:
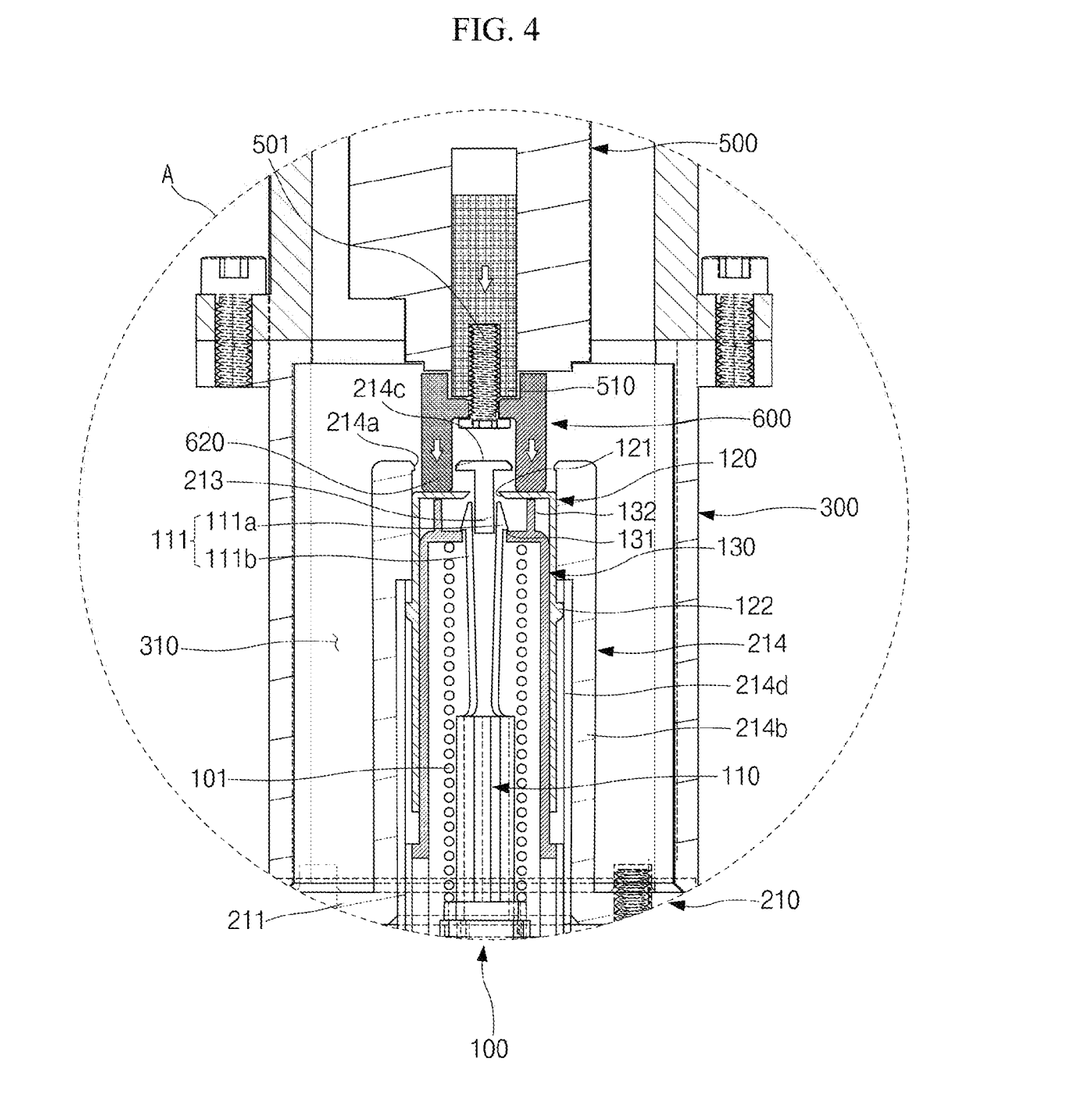
FIGS. 4 to 6 are enlarged cross-sectional views of a circle A shown in FIG. 3, which is for explaining a releasing operation relationship of a locking pin of an injection gadget.
Figure 5:
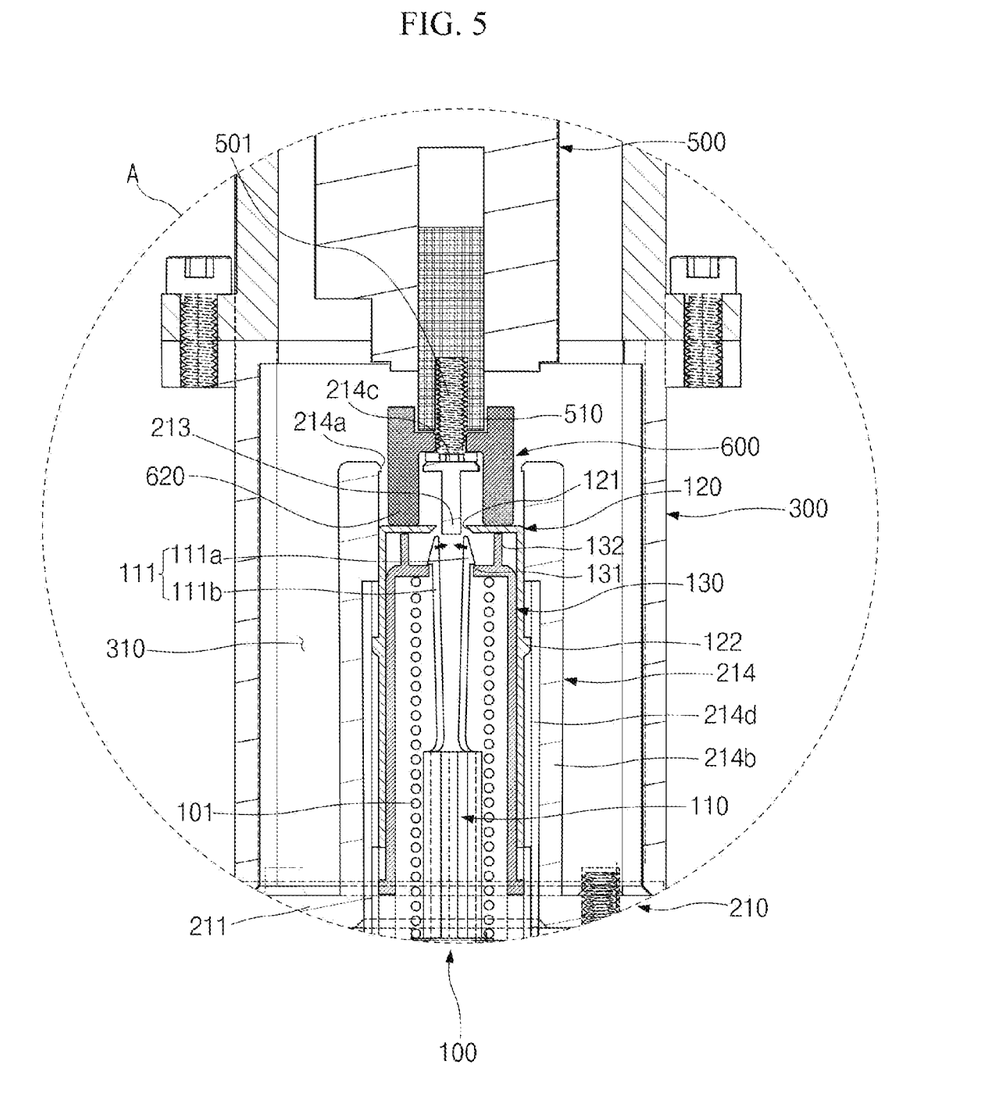
Figure 6:
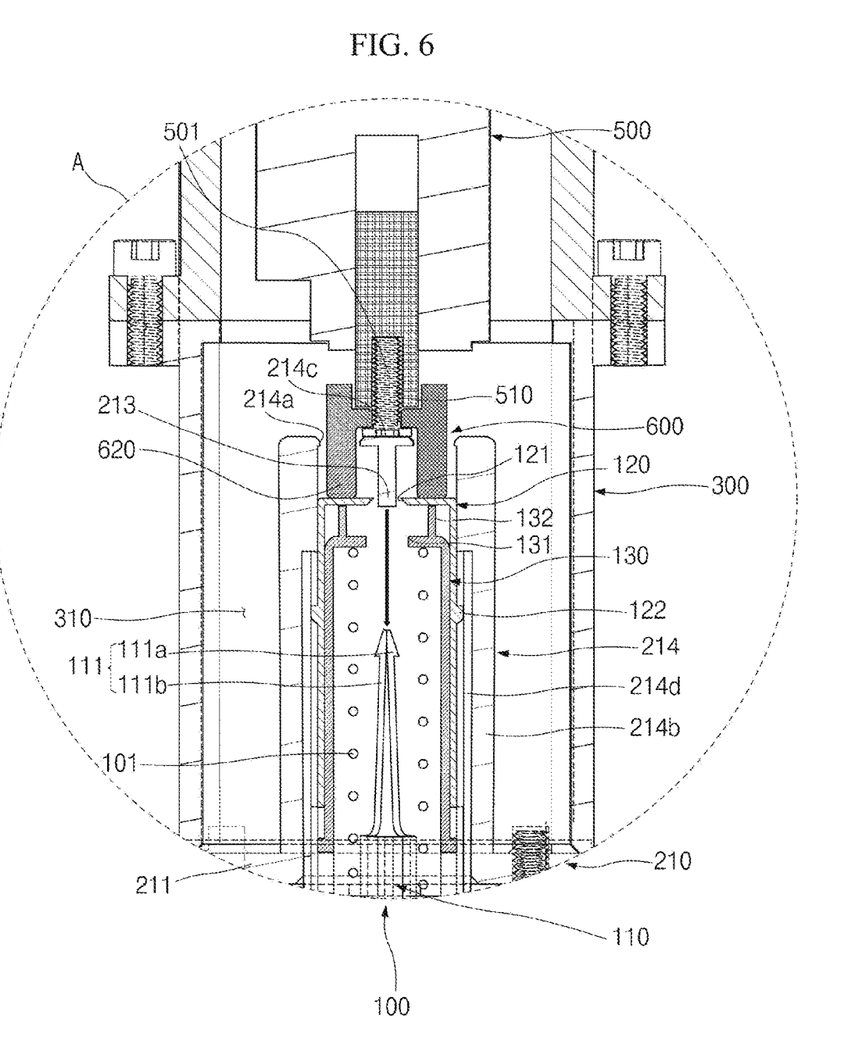

FIGS. 4 to 6 are enlarged cross-sectional views of a circle A shown in FIG. 3, which is for explaining a releasing operation relationship of a locking pin of an injection gadget.

Referring to FIG. 2 or FIG. 4, the pin holder 214 of the rear bracket 210 includes a hollow tube-shaped holder body 214*b* that is penetratingly connected to a center hole of the first flange portion 211, a pin support portion 214*c* that connects one side of an end of the holder body 214*b* and the other side thereof to each other, the pusher holes 214*a* that are formed at both sides of the pin support portion 214*c* to receive the bottom protrusions 620 of the pusher 600, and the locking pin 213 that protrudes from an inner bottom surface of the pin support portion 214*c* toward the injection assembly 100. Here, the locking pin 213 is integrally formed on the inner bottom surface of the pin support portion 214*c* of the pin holder 214 and protrudes vertically downward so that the locking pin 213 is kept fixed together with the rear bracket 210 including the pin holder 214.

That is, the locking pin 213 may be kept relatively fixed by the pin holder 214 and the rear bracket 210 despite the movement of the pusher 600.

When the linear actuator 500 is operated (e.g., lowering of the transfer shaft 510), a corresponding member (e.g., the movable cap 120) of the injection assembly 100 in contact with the bottom protrusions 620 of the pusher 600 may be moved and at the same time, the inner cap 130 positioned inside the movable cap 120 and the piston 110 positioned inside the inner cap 130 may be moved together with the movable cap 120, and therefore a releasing operation between the locking pin 213 and the piston 110 may be performed.

That is, referring to FIG. 4, in order to bring the piston 110 having the locking guides 111 into a locked state in a state before the present embodiment is used (e.g., a factory shipment state), the locking pin 213 passes through the pin hole 121 formed in the injection assembly 100, that is, the pin hole 121 of the movable cap 120, and is sandwiched between the four locking guides 111 having an elastic stress to be pinched toward the center of the injection assembly 100. At this time, the locking heads 111*a* of the four locking guides 111 are in an opened state so as to be spaced apart from each other. Here, the opened state means a state in which each of inner surfaces of the locking heads 111*a* is in contact with an outer surface of the locking pin 213 and is bent radially outward with respect to the center of the locking guides 111.

Here, the pin hole 121 is a hole having narrow upper sections and wide lower sections or a plate-like hole, and may avoid interference with the locking heads 111*a* described below.

In addition, the locking guides 111 are comprised of guide bars 111*b* that are cut or branched in four directions on the basis of a width section of the piston 110, and the locking heads 111*a* that are integrally formed at ends of the guide bars 111*b*.

The guide bars 111*b* are formed to be cut or branched from one end of the piston 110 of the injection assembly 100 positioned below the pin hole 121 so that the guide bars 111*b* are bent radially outward according to contact with the locking pin 213 or restored toward an inner center direction according to non-contact with the locking pin 213.

Each locking head 111*a* is formed at the end of the guide bar 111*b* so as to have a wedge shape or an arrow shape in which a downward inclined surface and a step are formed on an outer side of each guide bar 111*b*. Here, an inner surface of each locking head 111*a* maintains the same level as that of an inner surface of the guide bar 111*b*, and an outer side portion of each locking head 111*a* protrudes from an outer surface of the guide bar 111*b* and has a right angled triangle-like stopper formed to be pointed upward.

Such locking heads 111*a* may be caught by a rim of the trigger hole 131 of the inner cap 130 positioned inside the movable cap 120 inside the injection assembly 100 in response to a contact or non-contact situation with the locking pin 213, or may be brought into a free state.

The circular wall-shaped gap retaining portion 132 protruding longer than the length of each locking head 111*a* is formed above the inner cap 130, so that the locking heads 111*a* may not be in contact with a ceiling surface of an upper portion of the movable cap 120 and an interference factor with respect to the movement of the locking heads 111*a* may be eliminated.

In addition, in a state as shown in FIG. 4, the spring 101 inside the injection assembly 100 is compressed to accumulate an elastic force, and a lower end of the spring 101 is connected to the piston 110.

A sliding protrusion 122 in the form of a ring-shaped protrusion is formed on an outer circumferential surface of the movable cap 120.

A rail groove 214*d* recessed in a wall thickness direction of the pin holder 214 is formed on an inner circumferential surface of the pin holder 214 with respect to a position corresponding to the sliding protrusion 122, so that the rail grooves 214*d* may prevent the sliding protrusion 122 from being disassembled from an upper side of the pin holder 214 while it guides the movement of the sliding protrusion 122. Here, an upper end of the rail groove 214*d* serves as a latching jaw for restricting the upward movement of the sliding protrusion 122.

Accordingly, an upper end of the spring 101 is supported by the inner cap 130.

When the piston 110 is in a released state, a condition that the piston 110 can be strongly moved downward by the accumulated elastic force is satisfied.

However, as described above, since the locking heads 111*a* of the piston 110 are caught by the rim of the trigger hole 131 of the inner cap 130 before the movement of the pusher 600, the piston 110 is in an immovable locked state.

However, when the transfer shaft 510 of the linear actuator 500 is lowered due to the downward operation of the linear actuator 500, the pusher 600 also presses one end of the injection assembly 100 received in the pin holder 214 of the rear bracket 210, that is, the movable cap 120 to be in a state as shown in FIG. 5.

Thereafter, the locking heads 111*a* are deviated from the locking pin 213 so that the locking heads 111*a* and the guide bars 111*b* are pinched to be restored to their original states.

That is, the locking heads 111a are in a released state in which they are not caught by the rim of the trigger hole 131 of the inner cap 130.

Thereafter, as shown in FIG. 6, the piston 110 is moved by the strong elastic force of the spring 101 in the released state, and therefore an injection liquid is ejected through the injection needle due to the continued movement of the piston 110 while the injection needle (not shown) protrudes toward the lower outside of the injection assembly 100.

The injection gadget of the present embodiment described above may be very suitable for rescue robots for life-saving in situations such as natural disasters, wars, and the like, and developed and applied as a means for remotely checking a condition of a person who needs a rescue and taking emergency measures, prior to evacuation of the person who needs a rescue by the rescue robot.

The present embodiment may replace and apply the above-described process with and to the rescue robots so that releasing the locking pin and moving the piston may be realized by only one movement of the pusher, and therefore the locking pin may be released and at the same time relief activities (e.g., injecting an injection liquid) may be performed.

That is, the present embodiment may be very suitably used for rescue robots to be input in a situation where it is difficult to input lifesaving manpower such as in natural disasters or wars.

In addition, the present embodiment may prevent sliding or the like of the injection gadget in advance using the provided sensor.

As described above, the injection gadget according to the present invention may be an end-effector that can move the piston by a spring elastic force to inject an injection liquid while releasing the locking pin by only one pushing operation of the linear actuator, and therefore a compact and lightweight end-effector may be achieved, thereby relatively reducing the payload of the manipulator of the robot and improving the efficiency of use of power of the end-effector and the manipulator.

The injection gadget according to the present invention may be provided with a plurality of sensors (e.g., force sensors) for an injection site such as a muscular part of the femoral region or an object to be injected in front of the front bracket, so that the injection gadget may perfectly maintain a perpendicular state with respect to the object to be injected by estimating whether the object to be injected and the injection gadget are perpendicular to each other through a sensor value calculated when the front bracket is brought into contact with the object to be injected, thereby solving a sliding problem between the injection gadget and the object to be injected to accurately perform an injection on the object to be injected.

Although embodiments of the present invention have been described above with reference to the accompanying drawings, it is obvious that many modifications and changes may be made by those skilled in this art without departing from the scope of the invention. Therefore, the embodiments disclosed in the present invention are not intended to limit the technical spirit of the present invention, but are intended to describe the invention. The technical spirit of the present invention is not limited to such embodiments. The scope of the present invention must be defined by the following claims, and all equivalents thereof should be interpreted as being included in the technical spirit and scope of the present invention.

What is claimed is:

1. An injection gadget in which an injection needle is disposed inside an injection assembly, an injection liquid is provided between a cylinder and a piston of the injection assembly, and the piston is moved by an elastic force of a spring previously compressed inside the cylinder so that the injection needle protrudes to the outside of the injection assembly and the injection liquid is ejected, comprising:
    a bracket that replaceably mounts the injection assembly;
    a main body that is connected to the bracket and includes a first body space portion of which one side surface facing the bracket and the other side surface are open to pass through each other and a second body space portion that is disposed next to the first body space portion;
    a controller that is mounted in the second body space portion;
    a linear actuator that moves a transfer shaft in accordance with a control signal of the controller; and
    a pusher that is disposed between the linear actuator and the injection assembly, and transmits a force of the linear actuator toward the injection assembly so that a locking pin of the bracket is deviated from locking guides of the piston of the injection assembly.

2. The injection gadget of claim 1, wherein the main body is connected to an end-effector connector of a manipulator having a rescue robot structure, and a connector of the main body is electrically connected to the end-effector connector.

3. The injection gadget of claim 1, wherein the bracket includes a rear bracket and a front bracket which are disassembled or assembled for replacement of the injection assembly.

4. The injection gadget of claim 3, wherein the rear bracket of the bracket includes
    a pin holder that is inserted into the first body space portion and receives one end of the injection assembly,
    a first flange portion that is integrally formed on a rim of the pin holder, and
    a plurality of fastening pieces that protrude from a bottom surface of the first flange portion and have inclined steps.

5. The injection gadget of claim 4, wherein the front bracket of the bracket includes
    a second flange portion that includes fastening holes into which the fastening pieces are respectively inserted so that the second flange portion is caught by the inclined steps of the fastening pieces,
    an extension portion that extends from the second flange portion in a direction opposite to the first flange portion so as to mount the injection assembly, and
    a contact plate portion that is formed at an end of the extension portion and has a relatively large area as compared with the second flange portion.

6. The injection gadget of claim 5, wherein the contact plate portion includes a plurality of sensors that are provided on a surface of the contact plate portion facing an object to be injected and connected to the controller to detect a sensor value for estimating whether the object to be injected and the injection gadget are perpendicular to each other.

7. The injection gadget of claim 4, wherein the pin holder includes
    a hollow tube-shaped holder body that is penetratingly connected to a center hole of the first flange portion,
    a pin support portion that connects one side of an end of the holder body and the other side thereof to each other, pusher holes that are formed at both sides of the pin support portion to receive bottom protrusions of the pusher, and a locking pin that protrudes from an inner bottom surface of the pin support portion toward the injection assembly.

8. The injection gadget of claim 7, wherein the locking pin passes through a pin hole formed in the injection assembly, and is sandwiched between the locking guides having an elastic stress to be pinched toward a center of the injection assembly so that the piston having the locking guides is brought into a locked state.

9. The injection gadget of claim 8, wherein the locking guides include a plurality of guide bars that are cut or branched from one end of the piston of the injection assembly positioned below the pin hole so that the guide bars are bent radially outward according to contact with the locking pin or restored toward an inner center direction according to non-contact with the locking pin, and locking heads that are formed at ends of the guide bars so as to have an arrow shape, and the locking heads are caught by a rim of a trigger hole of an inner cap positioned inside the injection assembly in response to a contact or non-contact situation with the locking pin, or are brought into a free state.

\* \* \* \* \*